United States Patent [19]

Pickart

[11] Patent Number: 4,937,230

[45] Date of Patent: * Jun. 26, 1990

[54] METHOD OF HEALING WOUNDS IN HORSES

[75] Inventor: Loren R. Pickart, Bellevue, Wash.

[73] Assignee: ProCyte Corporation, Redmond, Wash.

[*] Notice: The portion of the term of this patent subsequent to May 12, 2004 has been disclaimed.

[21] Appl. No.: 128,738

[22] Filed: Dec. 4, 1987

Related U.S. Application Data

[63] Continuation-in-part of Ser. No. 694,430, Jan. 24, 1985, Pat. No. 4,760,051.

[51] Int. Cl.$^5$ .............................................. A61K 37/14
[52] U.S. Cl. .................................... 514/6; 514/16; 514/18; 514/947; 514/936; 514/886; 514/887; 424/638
[58] Field of Search ....................... 514/18, 6, 16, 947, 514/886, 887, 936; 424/638

[56] References Cited

U.S. PATENT DOCUMENTS

| | | | |
|---|---|---|---|
| 3,194,732 | 7/1965 | Neuhauser | 424/95 |
| 3,551,554 | 12/1970 | Herschler | 424/59 |
| 3,558,770 | 1/1971 | Gordon et al. | 424/80 |
| 3,758,682 | 9/1973 | Huber et al. | 514/6 |
| 3,767,784 | 10/1973 | Gluck | 424/445 |
| 3,832,338 | 8/1974 | Huber et al. | 514/6 |
| 4,022,888 | 5/1987 | Huber et al. | 514/6 |
| 4,167,945 | 9/1979 | Gottlieb | 424/101 |
| 4,177,261 | 12/1979 | Dietze et al. | 424/101 |
| 4,263,428 | 4/1981 | Apple et al. | 536/17 |
| 4,287,184 | 9/1981 | Young | 424/95 |
| 4,665,054 | 5/1987 | Pickart | 514/18 |
| 4,760,051 | 7/1988 | Pickart | 514/18 |
| 4,767,753 | 8/1988 | Pickart | 514/18 |

OTHER PUBLICATIONS

Pickart et al., "Growth-Modulating Tripeptide (glycylhistidylysine): Association with Copper and Iron in Plasma and Stimulation of Adhesive and Growth of Hepatoma Cells in Culture by Tripeptide-Metal Ion Complexes," J. Cell, Physiol., 102(2), pp. 129-139, 1980. (Cited in Chem. Abstracts, vol. 93: 1155m, 1980).

Williams et al., "Glycyl-L-Histidyl-L-Lysine, a Growth Promoting Factor for Human Cells," Cytobios., 27(105), pp. 19-25, 1980. (Cited in Chem. Abstracts, vol. 94:25451b, 1981).

Mochida Pharmaceutical Co., Ltd., "Antiinflammatory Injections Containing Superoxide Dismutase," Jpn. Kokai Tokyo Koho, 81 07,720, 27 Jan. 1981 (cited in Chem. Abstracts, vol. 94:145386f, 1981).

Kwa, "Glycyl-L-Histidyl-L-Lysine: Synthesis of Analogs and NMR Studies," Ph.D. Thesis, University of Washington, 1983.

Loker, "Synthesis of Blood Serum Peptide Cell Growth Factors," Ph.D. Thesis, University of Washington 1980.

Pickart, "The Biological Effects and Mechanism of Action of the Plasma Tripeptide Glycyl-L-Histidyl-L-Lysine," Lymphonkines, 8, pp. 425-446, 1983.

Poole et al., "Stimulation of Rat Peritoneal Mast Cell Migration by Tumor-Derived Peptides," Cancer Research, 43, pp. 5857-5861, 1983.

Raju et al., "Ceruloplasmin, Copper Ions, and Angiogenesis," Junci, 69(5), pp. 1183-1188, 1982.

Freedman et al., "Structure of the Glycyl-L-Histidyl-l-Lysine-Copper(II) Complex in Solution," Biochemistry, 21, pp. 4540-4544, 1982.

Kwa et al., "PMR Studies of CU(II) and Zn(II) Interaction with Glycyl-L-Histidyl-L-Lysine and Related Peptides," Peptides: Structure and Function, 8, pp. 805-808, 1983.

Perkins et al., "The Structure of a Copper Complex of the Growth Factor Glycyl-L-Histidyl-L-Lysine at 1.1 A Resolution," Inorganica Chimica Acta, 82, pp. 93—99, 1984.

Kimoto et al., "Enhancement of Antitumor Activity of Ascorbate Against Ehrlich Ascites Tumor Cells by the Copper: Glycylglycylhistidine Complex," Cancer Research, 43, pp. 824-828, 1963.

Sorenson, "Copper Complexes: A Physiological Approach to Treatment of Chronic Diseases," Comprehensive Therapy, 11(4), pp. 49-64, 1985.

Pickart et al., "Inhibition of the Growth of Cultured Cells and an Implanted Fibrosarcoma by Aroylhydrazone Analogs of the Gly-His-Lys-Cu(II) Complex," Biochem. Pharmacol., 32(24), pp. 3868-3871, 1983.

Pickart et al., "Growth-Modulating Plasma Tripeptide May Function By Facilitating Copper Uptake Into Cells," Nature, 288, pp. 715-717, 1980.

Natural Healing Annual 1986, p. 38 (Edit M. Bricklin, Prevention Magazine, Rodale Press, Emmaus, PA).

Pickart et al., "A Synthetic Tripeptide which Increases Survival of Normal Liver Cells, and Stimulates Growth in Hepatoma Cells," Biochem. Biophys. Res. Commun., 54(2), pp. 526-6, 1973.

Primary Examiner—Jacqueline M. Stone
Attorney, Agent, or Firm—Seed & Berry

[57] ABSTRACT

Methods are disclosed for enhancing the healing of a variety of wounds in horses. The methods generally comprise administering to the wound a therapeutically effective amount of a composition comprising GHL:Cu or a derivative thereof in combination with a physiologically acceptable carrier or diluent.

32 Claims, No Drawings

METHOD OF HEALING WOUNDS IN HORSES

CROSS-REFERENCE TO RELATED APPLICATION

This application is a continuation-in-part of pending U.S. Ser. No. 694,430 filed Jan. 24, 1985, now U.S. Pat. No. 4,760,051.

TECHNICAL FIELD

The present invention relates to pharmaceutical preparations in general, and more specifically, to the use of GHL:Cu and analogs or derivatives thereof within methods for healing a wide variety of wounds commonly found on horses.

BACKGROUND OF THE INVENTION

Wounds on horses are particularly difficult and slow to heal. In addition, the skin of horses is thin and difficult to effectively stitch together. Even after wounds are sewn, they often tend to break open again. The conditions normally found in stables, characterized by high ambient bacterial levels, are very conducive to transmitting infections to open or poorly scabbed-over wounds. Infections further slow down the healing process of the wounds.

Infected horse wounds have a tendency to form excessive amounts of scar tissue. This often produces disfiguring protrusions and swelling known as "proud flesh" Such swelling can markedly lower both the value and utility of the horse. In addition, poorly healed horse wounds often remain denuded of hair—a disfigurement that lowers the value of the animal.

Although a variety of compositions have been proposed as wound healing agents in this context, such as a combination of fish oil, turpentine, sulfuric and oleic acids, and kerosene, as described in U.S. Pat. No. 4,447,418, these compositions have not been significantly effective in promoting the healing of wounds. Therefore, there is a need in the art for improved compositions that are effective in (a) healing superficial wounds as well as infected wounds in horses, (b) reducing excessive accumulations of granulation tissue ("proud flesh"), (c) stimulating the growth of hair over wounds in horses, and (d) causing the rapid formation of protective scabs over wounds in horses. The present invention fulfills this need and further provides other related advantages.

DISCLOSURE OF THE INVENTION

Briefly stated, the present invention discloses a number of methods for enhancing the healing of a variety of wounds in horses, more fully described below. Within the present invention, the methods generally comprise administering to a horse wound a therapeutically effective amount of a composition comprising Glycyl-L-Histidy-L-Lysine: Copper(II) (referred to as "GHL:Cu") or a composition comprising a derivative of GHL:Cu having the general formula:

Copper (II), wherein R is selected from the group consisting of alkyl moieties containing from 1 to 18 carbon atoms, aryl moieties containing from 6 to 12 carbon atoms, alkoxy moieties containing from 1 to 12 carbon atoms, or wherein R is L-prolyl-L-valyl-L-phenylalanyl-L-valine or L-valyl-L-phenylalanyl-L-valine. In addition, the composition may comprise a derivative of GHL:Cu having the general formula:

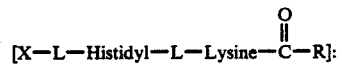

Copper (II), wherein X is glycyl-L-alanyl, glycyl-L-seryl, glycyl-L-valyl, or glycyl-L-glycyl, and wherein R is selected from the group consisting of alkyl moieties containing from 1 to 18 carbon atoms, aryl moieties containing from 6 to 12 carbon atoms, alkoxy moieties containing from 1 to 12 carbon atoms, or wherein R is L-prolyl-L-valyl-L-phenylalanyl-L-valine or L-valyl-L-phenylalanyl-L-valine.

In addition to the derivatives described above, other chemical modifications could be made to selectively alter the biological activity of the compositions of the present invention. By way of example, glycine may be replaced by a variety of other small amino acids, including alanine, serine and valine. Further, the copper(II) binding affinity of the molecule could be increased by the addition of an N-terminal amino acid, such as glycine, to convert Glycyl-L-Histidyl-L-Lysine to Glycyl-L-Glycyl-L-Histidyl-L-Lysine. In addition, glycine could be added to a derivative as described above to create the corresponding tetrapeptide. Further, the binding affinity for copper(II) of the imadazole group in the histidyl residue could be modified by substitution of 3-methylhistidine or by extending the lysyl side chain by adding additional carbon atoms to the chain.

These and other aspects of the invention will become evident upon reference to the following detailed description.

BEST MODE FOR CARRYING OUT THE INVENTION

GHL:Cu and derivatives thereof described herein are effective in enhancing the healing of (a) saddle sores; (b) cuts and abrasions, often caused by barbed wire; (c) infected wounds of various types; (d) fly bites; (e) puncture wounds; (f) rope burns; (f) full-thickness skin loss; (g) ulcerating pressure-induced wounds; and (h) suture line dehiscence. In addition, the compositions described herein are also effective in stimulating the growth of hair over wounds in horses, and in reducing excessive accumulations of granulation tissue ("proud flesh").

GHL:Cu and the derivatives described herein may also be used in combination with other factors to improve other facets of healing. In this manner, an enhanced healing effect may be obtained that provides an improved clinical efficacy. While the compositions described herein stimulate a spectrum of healing actions, clinical wounds often vary considerably in their properties and healing patterns, leading one to utilize a combination of a composition described herein and another factor. For example, nerve growth regeneration is defective in many injuries, and therefore one might add a specific nerve growth factor to GHL:Cu or a derivative thereof to enhance nerve regrowth into the injured area.

Examples of reported factors with other healing properties include Lysyl-proline, epidermal growth factor, fibroblast growth factor, nerve growth factor, transforming growth factors alpha and beta, the Interleukins, angiogenic growth factors, heparin, fibronectin, fibrin, platelet-derived growth factor, enzymatic superoxide dismutase, extracts of blood or factors from blood, and other similar factors.

Within the present invention, one may utilize a ratio of GHL or a derivative thereof to copper of 1:1, 2:1 or less. Within a preferred embodiment, optimal healing occurs with a ratio of 0.5–0.75 copper atoms per GHL molecule. Copper in molar excess to GHL (>1.00) is loosely bound and may delay the healing process since it is believed that free copper salts attract inflammatory cells such as neutrophils.

The rapidity of reestablishment of a biological coverage on the wound surface is a critical element in the healing prognosis. Natural open wounds are first covered by a blood and plasma exudate which dries to form the initial "scab" that covers the wound. This scabby layer forms a short-term protective coverage from outside elements while healing proceeds under this layer In wounds treated with GHL:Cu and derivatives thereof, there is a greater liquid (serum-like) exudate over the wounds. The treated wounds have a "wetter" appearance, and the scabby layer that forms over the wound is substantially thicker. The first covering over a fresh wound is a thin covering formed from the blood and serum that dry over the wound. Since it often takes several days before a thick biological covering forms over a wound, the present invention is valuable in protecting the wound from infection and further blood loss, through the rapid generation of a protective scab. Healing can then take place beneath the protective scab. This is especially important in the case of horse wounds where scab formation is normally slow and infection is common due to environmental conditions.

Pharmaceutical preparations containing GHL:Cu and derivatives thereof may be formulated as liquids, lotions, creams or gels. An effective dosage of the compositions described herein for use within the present invention is approximately 0.1% to about 5% by weight of GHL:Cu or a derivative thereof. A preferred range in this regard is about 0.1% to 1% by weight, with 0.1% to 0.4% being particularly preferred.

In another embodiment of the present invention, the pharmaceutical preparation may further contain from about 1% to about 10% by weight of an emulsifying or surface active agent, with 3% to 6% being preferred. Non-ionic surface active agents are preferred for the purposes of the present invention. Examples of suitable non-ionic surface active agents include nonylphenoxypolyethoxy ethanol (Nonoxynol-9), polyoxyethylene oleyl ether (Brij-97), various polyoxyethylene ethers (Tritons), and block copolymers of ethylene oxide and propylene oxide of various molecular weights (Pluronic 68 for example).

In addition to, or in place of, the emulsifying or surface active agent, the pharmaceutical preparation may further contain from about 1% to 20% of a penetrating agent. Examples of suitable penetrating agents are dimethyl sulfoxide (DMSO) and urea. In the case of a pharmaceutical preparation formulated as a liquid for topical application, the concentration of a penetrating agent such as DMSO may comprise from about 30% to 80% of the pharmaceutical preparation.

The balance of the pharmaceutical preparation comprises an inert, physiological acceptable carrier or diluent. This carrier or diluent should not substantially interact with the active ingredients nor reduce the effectiveness of the GHL:Cu or derivatives thereof. Suitable carriers or diluents include, but are not limited to, water, physiological saline, bacteriostatic saline (saline containing 0.9 mg/ml benzyl alcohol), and petrolatum based creams (USP hydrophylic ointments and similar creams; Unibase, Parke-Davis, for example).

The following preparations are exemplary of suitable pharmaceutical preparations as described above:

| (A) | GHL:Cu | 0.4% (w/w) |
|---|---|---|
|  | DMSO | 6.0% |
|  | Unibase | 93.6% |
| (B) | GHL:Cu | 0.4% (w/w) |
|  | Nonoxynol-9 | 3.0% |
|  | Unibase | 96.6% |
| (C) | GHL:Cu | 0.4% (w/v) |
|  | Bacteriostatic saline | 30.0 mL |
| (D) | GHL-Octyl Ester:Cu | 0.4% (w/w) |
|  | DMSO | 6.0% |
|  | Unibase | 93.6% |

Topical administration of the pharmaceutical preparations of the present invention may be accomplished by applying a small amount of the composition directly to the wound and the area surrounding the wound. A quantity sufficient to cover the area of the wound is effective. Treatment may be influenced by the severity of the wound, and will generally be repeated as the progress of healing indicates. In general, the compositions are initially applied approximately 2–3 times per day. It may be preferable to reduce the number of administrations as treatment continues, or to decrease the concentration of GHL-Cu or derivative thereof over the period of treatment. A number of exemplary treatment schedules are set forth in the examples.

Alternative methods of applying the compositions within the present invention include spraying onto or the subcutaneous injection of solutions of GHL:Cu or derivatives thereof into the wound and the area surrounding the wound, in acceptable pharmaceutical preparations (such as a combination of GHL:Cu or a derivative thereof and physiological saline).

To summarize the examples that follow, Examples 1–4 illustrate the synthesis of selected GHL derivatives. Example 1 describes the synthesis of Glycyl-L-Histidyl-L-Lysine benzyl ester:Copper(II). Example 2 demonstrates the synthesis of Glycyl-L-Histidyl-L-Lysine n-octyl ester: Copper(II). Example 3 illustrates (A) the synthesis of Glycyl-L-Histidyl-L-Lysine n-stearyl ester:Copper(II) and (B) its synthesis by an alternative procedure. Based upon either procedure, one skilled in the art could substitute n-palmityl alcohol (16 carbons) for the n-stearyl alcohol (18 carbons) to yield Glycyl-L-Histidyl-L-Lysine n-palmityl ester:Copper(II). Example 4 illustrates the synthesis of Glycyl-L-Histidyl-L-Lysyl-L-Prolyl-L-Phenylalanyl-L-Valine:Copper(II) and Glycyl-L-Histidyl-L-Lysyl-L-Valyl-L-Phenylalanyl-L-Valine:Copper(II). The remaining examples (5–12) illustrate the use of GHL:Cu and selected derivatives thereof to heal a variety of wounds in horses.

The following examples are offered by way of illustration and not by way of limitation.

EXAMPLES

Sources of Chemicals

Chemicals and peptide intermediates utilized in the following examples may be purchased from a number of suppliers, for example Sigma Chemical Co., St. Louis, Mo.; Peninsula Laboratories, San Carlos, Calif.; Aldridge Chemical Company, Milwaukee, Wis.; Vega Biochemicals, Tucson, Ariz.; Pierce Chemical Co., Rockford, Ill.; Research Biochemicals, Cleveland, Ohio: Van Waters and Rogers, South San Francisco, Calif.; and Bachem, Inc., Torrance, Calif.

Preparation of GHL:Cu for Use on Horses

Glycyl-L-Histidyl-L-Lysine (GHL) was purified by dissolving in glass distilled water at 50–200 mg/mL and centrifuging at 20,000×g for 1 hour at 3° C. This treatment removes poorly water soluble material remaining from the synthetic procedures. The supernatant solution is then passed over a Sephadex G-10 or G-15 column eluted with distilled water. The main peak which elutes behind the void volume is collected and lyophylized.

GHL:Cu at a molar ratio of 1:1 was prepared by combining Glycyl-L-Histidyl-L-Lysine with an equimolar amount of copper(II) chloride and neutralization to about pH 7.0. The GHL:Cu (1:1) was purified by passage through a Sephadex G-10 column as described for the GHL. GHL:Cu at molar ratios other than 1:1 was prepared by mixing the required weights of purified GHL and purified GHL:Cu (1:1).

EXAMPLE 1

Synthesis of Glycyl-L-Histidyl-L-Lysine benzyl ester:Copper (II).

$N^e$-benzyloxycarbonyl-L-lysine benzyl ester was dissolved in 1:1 hexane-ethyl acetate and coupled to $N^a$-t-butyloxycarbonyl-Nim-benzyloxycarbonyl-L-histidine using dicyclohexylcarbodiimide as a coupling agent. Sodium bicarbonate (10%) was added and the product was extracted into the organic layer. The product, $N^a$-t-butyloxycarbonyl-Nim-benzyloxycarbonyl-L-histidyl-$N^e$-benzyloxycarbonyl-L-lysine benzyl ester, was crystalized from solution. The N-terminal group of the blocked dipeptide was removed by stirring in 50% trifluoroacetic acid in dichloromethane for 30 minutes, then vacuum evaporated.

The product, $N^{im}$-benzyloxycarbonyl-L-histidyl-$N^e$-benzyloxycarbonyl-L-lysine benzyl ester, was coupled to benzyloxycarbonyl-L-glycine with dicyclohexylcarbodiimide as a coupling agent. Blocking groups were removed by catalytic hydrogenation using 10% palladium on carbon in glacial acetic acid. After lyophylization, the product, Glycyl-L-Histidyl-L-Lysine benzyl ester, was dissolved in water and purified by ion-exchange chromatography on Dowex 50 X-4 cation-exchange resin and elution with 0.1M ammonium hydroxide, the eluate being immediately neutralized with acetic acid. A further passage through an anion-exchange column, BioRex 63, at neutral pH removed breakdown products with free carboxylic acid groups.

The Glycyl-L-Histidyl-L-Lysine benzyl ester was dissolved in water with equimolar Copper(II) acetate added. The pH was raised to neutrality with sodium hydroxide. The solution was centrifuged at 20,000×g for 1 hour at 3° C. to remove poorly soluble material. The supernatant solution was lyophylized to obtain Glycyl-L-Histidyl-L-Lysine benzyl ester:Copper(II).

EXAMPLE 2

Synthesis of Glycyl-L-Histidyl-L-Lysine octyl ester:Copper (II).

A mixture of $N^e$-benzyloxycarbonyl-L-lysine, n-octanol, benzene, and p-toluenesulfonic acid monohydrate was refluxed overnight using a Dean-Stark trap to remove water. After cooling, dry ethyl ether was added. The solution was then allowed to precipitate at 0° C. overnight. A portion of the precipitate solid was added to 50 mL of potassium carbonate solution and 50 mL of dichloromethane. After extraction, the layers were separated and the organic phase was washed with water and brine, then dried with anhydrous magnesium sulfate. Filtration, evaporation and purification by flash column chromatography gave n-octyl $N^e$-benzyloxycarbonyl-L-lysine. The product was dissolved in tetrahydrofuran and mixed with $N^a$-t-butyloxycarbonly-$N^{im}$-benzyloxycarbonyl-L-histidine, isobutyl chloroformate and N-methylmorpholine. After evaporation, water and ethyl acetate were added. The product was extracted into the organic phase, which was dried with anhydrous magnesium sulfate. Filtration, evaporation, and purification by flash column chomatography gave n-octyl $N^a$-t-butyloxy-carbonyl-$N^{im}$-benzyloxycarbonyl-L-histidinyl-$N^e$-benzyloxy-carbonyl-L-lysinate.

The product was dissolved in 50% trifluoroacetic acid in dichloromethane for 30 minutes, then evaporated, forming n-octyl $N^{im}$-benzyloxycarbonyl-L-histidyl-$N^e$-benzyl-oxycarbonyl-L-lysinate. This was dissolved in tetrahydrofuran, and isobutyl chloroformate, N-methylmorpholine and benzyloxycarbonylglycine were added to form n-octyl benzyl-oxycarbonylglycyl-$N^{im}$-benzyloxycarbonyl-L-histidyl-$N^e$-benzyl oxycarbonyl-L-lysinate. This was dissolved in glacial acetic acid and hydrogenated overnight.

The resultant n-octyl ester of Glycyl-L-Histidyl-L-Lysine was converted to the Copper(II) complex by dissolving water and mixing with equimolar Copper(II) acetate. The pH was raised to neutrality with sodium hydroxide. The solution was centrifuged at 20,000×g for 1 hour at 3° C. to remove poorly soluble material The supernatant solution was lyophylized to obtain Glycyl-L-Histidyl-L-Lysine benzyl octyl:Copper(II).

EXAMPLE 3

A. Synthesis of Glycyl-L-Histidyl-L-Lysine n-stearyl ester:Copper (II).

A mixture of $N^e$-benzyloxycarbonyl-L-lysine, n-stearyl alcohol, benzene, and p-toluenesulfonic acid monohydrate was refluxed overnight using a Dean-Stark trap to remove water. After cooling, dry propyl ether was added to increase the total volume sixfold. The product was allowed to precipitate at 0° C. overnight and filtered A portion of the precipitate solid was added to 50 mL of potassium carbonate solution and 50 mL of dichloromethane. After extraction, the layers were separated and the organic phase was washed with water and brine, then dried with anhydrous magnesium sulfate. Filtration, evaporation and purification by flash column chromatography gave n-stearyl $N^e$-benzyloxycarbonyl-L-lysine The product was dissolved in tetrahydrofuran and mixed with $N^a$-t-butylloxycarbonyl-$N^{im}$-benzyloxycarbonyl-L-histidine, isobutyl chloroformate and N-methylmorpholine. After evaporation, water and propyl acetate were added. The product was extracted into the organic phase, which was dried with anhydrous magnesium sulfate. Filtration, evaporation, and purification by flash column chromatography gave n-stearyl $N^a$-t-butyl-oxycarbonyl-$N^{im}$-benzyloxycarbonyl-L-histidyl-$N^e$-benzyloxycarbonyl-L-lysinate.

The product was dissolved in 50% trifluoroacetic acid in dichloromethane for 30 minutes, then evaporated, forming n-stearyl $N^{im}$-benzyloxycarbonyl-L-histidyl-$N^\epsilon$-benzyl-oxycarbonyl-L-lysinate. This was dissolved in tetrahydrofuran, and isobutyl chloroformate, N-methylmorpholine and benzyloxycarbonylglycine were added to form n-stearyl benzyloxycarbonylglycyl-$N^{im}$-benzyloxycarbonyl-L-histidy-$N^\epsilon$-benzyloxy-carbonyl-L-lysinate. The product was dissolved in 50% trifluoroacetic acid in dichloromethane for 30 minutes, then evaporated, forming the n-stearyl ester of Glycyl-L-Histidyl-L-Lysine.

The resultant n-stearyl ester of Glycyl-L-Histidyl-L-Lysine was converted to the Copper(II) complex by dissolving water and mixing with equimolar Copper(II) acetate. The pH was raised to neutrality with sodium hydroxide. The solution was centrifuged at 20,000×g for 1 hour at 3° C. to remove poorly soluble material. The supernatant solution was lyophilyzed to obtain Glycyl-L-Histidyl-L-Lysine benzyl stearyl:Copper(II).

By substituting n-palmityl alcohol for the n-stearyl alcohol, Glycyl-L-Histidyl-L-Lysine n-palmityl ester may be similarly synthesized.

B. Alternative Synthesis of Glycyl-L-Histidyl-L-Lysine n-stearyl ester:Copper (II).

A mixture of $N^\epsilon$-benzyloxycarbonyl-L-lysine, n-stearyl alcohol, benzene, and p-toluenesulfonic acid monohydrate was refluxed overnight using a Dean-Stark trap to azeotropically remove the evolved water. After cooling to room temperature and then adding dry ethyl ether, n-stearyl $N^\epsilon$-benzyloxycarbonyl-L-lysinate p-toluenesulfonate salt is collected by filtration, treated with 2M aqueous potassium bicarbonate solution, and extracted into dichloromethane. Evaporation gives the free amine, which is redissolved in dry tetrahydrofuran (THF) and added to a stirring solution of $N^a$-t-butyloxycarbonyl-$N^{im}$-benzyloxy-carbonyl-L-histidine, N-methylmorpholine, and isobutyl chloroformate in dry THF at $-15°$ C.

The resulting fully protected dipeptide ester is treated with 1/1 trifluoroacetic acid/dichloromethane at room temperature, neutralized with saturated aqueous sodium bicarbonate solution, and extracted into ethyl acetate. Evaporation gives the partially deblocked dipeptide, which is redissolved in dry THF and added to a stirring solution of benzyloxycarbonylglycine, N-methylmorpholine, and isobutyl chloroformate in dry THF at $-15°$ C. The formed, fully protected tripeptide ester is totally deblocked by treatment with hydrogen gas in glacial acetic acid at room temperature in the presence of Pd-C catalyst Filtration, evaporation and purification on a microcrystaline cellulose column followed by lyophylization give the desired tripeptide ester as its triacetate salt.

The resulting molecule n-stearyl ester of Glycyl-L-Histidyl-L-Lysine was converted to the Copper(II) complex by dissolving water and mixing with equimolar Copper(II) acetate. The pH was raised to neutrality with sodium hydroxide. The solution was centrifuged at 20,000×g for 1 hour at 3° C. to remove poorly soluble material The supernatant solution was lyophylized to obtain Glycyl-L-Histidyl-L-Lysine benzyl stearyl:Copper(II).

By substituting n-palmityl alcohol for the n-stearyl alcohol, Glycyl-L-Histidyl-L-Lysine n-palmityl ester may be similarly synthesized.

EXAMPLE 4

Synthesis of Glycyl-L-Histidyl-L-Lysyl-L-Prolyl-L-Phenylalanyl-L-Valine:Copper(II) and Glycyl-L-Histidyl-L-Lysyl-L-Valyl-L-Phenylalanyl-L-Valine:Copper(II).

These peptides are synthesized by standard solid phase methods common to the peptide field (J. Stewart and J. Young, Solid Phase peptide Synthesis, pierce Chemical Company, 1984). Briefly stated, Boc-Val-0-Resin was sequently coupled with other blocked amino acids using dicyclohexylcarbodiimide as a reaction agent. Protected amino acids, resins for solid phase synthesis, and coupling agents were obtained from Peninsula Laboratories, San Carlos, Calif. Blocked amino acids are added in sequential order to obtain the desired peptide. The final peptide is deblocked using hydrogen fluoride. The final peptide product is dissolved in 0.5% acetic acid and purified by passage through a Sephadex G-15 column equilibrated with the same solvent. Addition of equimolar Copper(II) acetate, followed by neutralization and lyophylization gives the active molecule.

EXAMPLE 5

Saddle Sores From Fly Bites

History: Horse A suffered from fly bites which became infected and developed into irritating raised nodules located on the back in the saddle region over a period of 8 weeks. Treatment with traditional antibiotics for 6 weeks resulted in no resolution of the condition.

Treatment: A cream base containing 0.4% GHL-CU and 6% DMSO was applied twice/daily to the nodules. Within 4-5 days, softening of the nodules occurred along with diminishment of irritation and inflammation. Total healing occurred within 10-14 days.

EXAMPLE 6

Denuded Area After Injury (1) History: Approximately 2 months following wounding (lower leg, cause unspecified) healing occurred in horse B with poor regrowth of hair. The affected area measured approximately 2 square inches Treatment: A cream base containing 0.4% GHL-CU and 6% DMSO was applied to the denuded area 3-4 times/week. Substantial hair growth was noted after treatment for approximately 2-3 weeks.

(2) History: An ulcerative sore on the back of Horse C below the saddle horn area (withers) was treated by a veterinarian using antibiotics and an antibacterial spray. Proper healing failed to occur. Hair was absent from the partially healed sore.

Treatment: A cream base consisting of 0.4% GHL-CU and 6% DMSO was applied 1-2 times/day. Within 3 weeks, the infected ulcerative area resolved and hair was noted to be covering the wound.

EXAMPLE 7

Puncture Wounds

History: A puncture wound of unknown origin occurred to the upper leg of horse D. No traditional therapy (antibiotics) was used prior to treatment.

Treatment: A cream base containing 0.4% GHL-CU and 3% DMSO was applied to the wound site shortly after the wound was discovered. The wound did not become infected and healed within a few days. The treatment was performed twice/day.

EXAMPLE 8

Barbed-Wire Cuts/Gashes (1) History: The skin of the hoof area of horse E was badly torn from barbed-wire. Treatment by a veterinarian for 1 month with antibiotics failed to heal the area. Infection resulted in a continuous breakdown of the wound.

Treatment: A cream base containing 0.4% GHL:CU and 6% DMSO was applied to the area 2 times/day. After 5 days, the wound scabbed over. Treatment was halted and the area continued to heal. By 3 weeks after treatment, an examination of the wound found no evidence of infection, and healthy pink flesh was present under the remaining scab.

(2) History: A 33-year-old horse (horse F) received a serious barbed wire wound to the lower leg directly into the cleft of the hoof. The wound area was ripped open, thereby dividing the hoof. Treatment with Iodine and peroxide resulted in no improvement over a 2-week period.

Treatment: A cream base with 0.4% GHL-CU and 6% DMSO was applied 1-2 times/day. A new scab formation took place within a few days with reduction in the wound size. Treatment continued over 2 weeks, with a continuation of wound reduction and scab covering. Almost total healing occurred within 4 weeks.

(3) History: A very deep barbed-wire induced gash on the upper rear leg of horse G was originally treated with antibiotics and closed with stitches. The wound broke open (dehiscence) after a few days at which time the wound measured approximately 6 inches long and 1 inch wide. Treatment with an antibacterial agent (0.2% nitrofurosone) was ineffective.

Treatment: A cream containing 0.4% GHL-CU and 6% DMSO was applied for 2 weeks (1-2 times/day). A scab formed quickly over the open, raw tissue. Within 4 weeks, the wound had begun to close and appeared healthy. When the scab was removed during cleaning, it was noted that the gash had granulated considerably.

EXAMPLE 9

Rope Burn

History: Horse H had a severe rope burn to the rear ankle area. The rope burn had removed all hair and skin. A veterinarian treated the burn with antibiotics and a nitrofurosone ointment. The scab was removed daily with washing. The injury responded, although quite slowly.

Treatment: A cream base with 0.4% GHL-CU and 6% DMSO was applied to the burn 2 times/day. The scab was left on the area during the treatment period. The wound healed up within a week, and hair grew back over the area.

EXAMPLE 10

Full-Thickness Skin Loss

History: Horse I suffered from a traumatic injury to the anterior mid-calf aspect of the rear leg, caused by striking a fence while jumping. A flap of skin initially remained over the approximately 2.5 inch diameter wound. The leg was bandaged for a brief time, and the dead skin flap removed within 10 days post-injury. The leg appeared swollen and inflamed.

Treatment: A cream base containing 0.4% GHL-octyl ester Cu and 6% DMSO was applied to the wound area 2 times/day for 2 weeks, at which time a scab had formed over the area and the wound size had been reduced by almost 50%. Inflammation and swelling had also diminished. Using continued treatment (1 time/day) over the following week, the wound continued to decrease in size.

EXAMPLE 11

Ulcerating Pressure-induced Injury

History: A 12-year-old thoroughbred (horse J) developed a large ulcer (2 inch diameter) on top of the withers (back beneath saddle horn area) A veterinarian treated the wound with antibiotics and an antibacterial spray. Infection was present and did not resolve. The wound continued to be large and inflamed after 3–4 months Treatment: A cream containing 0.4% GHL:Cu with 6% DMSO was applied 1–2 times/day. The old scab fell off after a few days and was replaced by a new scab. After 2 weeks, the infection cleared up and ulceration began to be replaced by a skin covering. Shortly thereafter, hair began growing over the area. Approximately 1 month after beginning treatment, the ulcerative injury had resolved totally.

EXAMPLE 12

Excessive Accumulation of Granulation Tissue

History: An accumulation of unsightly granulation tissue or granuloma (known as "proud flesh") was present over a poorly healed wound (sight unspecified) in horse K. Typically, proud flesh often accompanies an insufficiently healing wound, appearing bubbly, swollen and nodular.

Treatment: A cream base containing 0.4% GHL:CU and 3% DMSO was applied for a period of one month, with a notable reduction in swelling and improved appearance.

From the foregoing, it will be appreciated that, although specific embodiments of the invention have been described herein for purposes of illustration, various modifications may be made without deviating from the spirit and scope of the invention. Accordingly, the invention is not to be limited except as by the appended claims

I claim:

1. A method of enhancing the healing of superficial wounds in horses, comprising:
administering to a superficial horse wound a therapeutically effective amount of a composition comprising Glycyl-L-Histidyl-L-Lysine: Copper(II) or a derivative of Glycyl-L-Histidyl-L-Lysine: Copper(II) having the general formula:

wherein R is selected from the group consisting of alkyl moieties containing from 1 to 18 carbon atoms, aryl moieties containing from 6 to 12 carbon atoms, alkoxy moieties containing from 1 to 18 carbon atoms, or wherein R is L-prolyl-L-valyl-L-phenylalanyl-L-valine or L-valyl-L-phenylalanyl-L-valine.

2. The method of claim 1 wherein said composition includes an emulsifying or surface active agent.

3. The method of claim 1 wherein said composition includes a penetrating agent.

4. The method of claim 1 wherein said composition is admixed with a pharmaceutically acceptable cream, lotion, gel or liquid vehicle prior to being administered.

5. A method of enhancing the healing of superficial wounds in horses, comprising:
administering to a superficial horse wound a therapeutically effective amount of a composition comprising a derivative of Glycyl-L-Histidyl-L-Lysine: Copper(II) having the general formula:

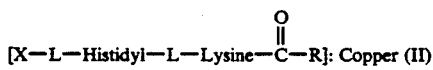

wherein X is glycyl-L-alanyl, glycyl-L-seryl, glycyl-L-valyl, or glycyl-L-glycyl, and wherein R is selected from the group consisting of alkyl moieties containing from 1 to 18 carbon atoms, aryl moieties containing from 6 to 12 carbon atoms, alkoxy moieties containing from 1 to 18 carbon atoms, or wherein R is L-prolyl-L-valyl-L-phenylalanyl-L-valine or L-valyl-L-phenylalanyl-L-valine.

6. The method of claim 5 wherein said composition includes an emulsifying or surface active agent.

7. The method of claim 5 wherein said composition includes a penetrating agent.

8. The method of claim 5 wherein said composition is admixed with a pharmaceutically acceptable cream, lotion, gel or liquid vehicle prior to being administered.

9. A method of enhancing the healing of infected wounds in horses comprising:
administering to an infected horse wound a therapeutically effective amount of a composition comprising Glycyl-L-Histidyl-L-Lysine: Copper(II) or a derivative of Glycyl-L-Histidyl-L- Lysine: Copper(II) having the general formula:

wherein R is selected from the group consisting of alkyl moieties containing from 1 to 18 carbon atoms, aryl moieties containing from 6 to 12 carbon atoms, alkoxy moieties containing from 1 to 18 carbon atoms, or wherein R is L-prolyl-L-valyl-L-phenylalanyl-L-valine or L-valyl-L-phenylalanyl-L-valine.

10. The method of claim 9 wherein said composition includes an emulsifying or surface active agent.

11. The method of claim 9 wherein said composition includes a penetrating agent.

12. The method of claim 9 wherein said composition is admixed with a pharmaceutically acceptable cream, lotion, gel or liquid vehicle prior to being administered.

13. A method of enhancing the healing of infected wounds in horses, comprising:
administering to an infected horse wound a therapeutically effective amount of a composition comprising a derivative of Glycyl-L-Histidyl-L-Lysine: Copper(II) having the general formula:

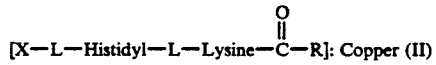

wherein X is glycyl-L-alanyl, glycyl-L-seryl, glycyl-L-valyl, or glycyl-L-glycyl, and wherein R is selected from the group consisting of alkyl moieties containing from 1 to 18 carbon atoms, aryl moieties containing from 6 to 12 carbon atoms, alkoxy moieties containing from 1 to 18 carbon atoms, or wherein R is L-prolyl-L-valyl-L-phenylalanyl-L-valine or L-valyl-L-phenylalanyl-L-valine.

14. The method of claim 13 wherein said composition includes an emulsifying or surface active agent.

15. The method of claim 13 wherein said composition includes a penetrating agent.

16. The method of claim 13 wherein said composition is admixed with a pharmaceutically acceptable cream, lotion, gel or liquid vehicle prior to being administered.

17. A method of reducing excessive accumulations of granulation tissue in horses, comprising:
administering to an affected area in the horse a therapeutically effective amount of a composition comprising Glycyl-L-Histidyl-L-Lysine: Copper(II), or a derivative of Glycyl-L-Histidyl-L-Lysine: Copper(II) having the general formula:

wherein R is selected from the group consisting of alkyl moieties containing from 1 to 18 carbon atoms, aryl moieties containing from 6 to 12 carbon atoms, alkoxy moieties containing from 1 to 18 carbon atoms, or wherein R is L-prolyl-L-valyl-L-phenylalanyl-L-valine or L-valyl-L-phenylalanyl-L-valine.

18. The method of claim 17 wherein said composition includes an emulsifying or surface active agent.

19. The method of claim 17 wherein said composition includes a penetrating agent.

20. The method of claim 17 wherein said composition is admixed with a pharmaceutically acceptable cream, lotion, gel or liquid vehicle prior to being administered.

21. A method of reducing excessive accumulations of granulation tissue in horses, comprising:
administering to an affected area in the horse a therapeutically effective amount of a composition comprising a derivative of Glycyl-L-Histidyl-L-Lysine: Copper(II) having the general formula:

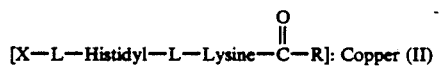

wherein X is glycyl-L-alanyl, glycyl-L-seryl, glycyl-L-valyl, or glycyl-L-glycyl, and wherein R is selected from the group consisting of alkyl moieties containing from 1 to 18 carbon atoms, aryl moieties containing from 6 to 12 carbon atoms, alkoxy moieties containing from 1 to 18 carbon atoms, or wherein R is L-prolyl-L-valyl-L-phenylalanyl-L-valine or L-valyl-L-phenylalanyl-L-valine.

22. The method of claim 21 wherein said composition includes an emulsifying or surface active agent.

23. The method of claim 21 wherein said composition includes a penetrating agent.

24. The method of claim 21 wherein said composition is admixed with a pharmaceutically acceptable cream, lotion, gel or liquid vehicle prior to being administered.

25. A method of enhancing the formation of protective scabs over wounds in horses, comprising:
administering to a horse wound a therapeutically effective amount of a composition comprising Glycyl-L-Histidyl-L-Lysine: Copper(II) or a derivative of Glycyl-L-Histidyl-L-Lysine: Copper(II) having the general formula:

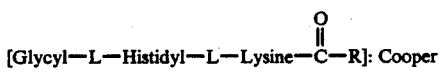 (II)

wherein R is selected from the group consisting of alkyl moieties containing from 1 to 18 carbon atoms, aryl moieties containing from 6 to 12 carbon atoms, alkoxy moieties containing from 1 to 18 carbon atoms, or wherein R is L-prolyl-L-valyl-L-phenylalanyl-L-valine or L-valyl-L-phenylalanyl-L-valine.

26. The method of claim 25 wherein said composition includes an emulsifying or surface active agent.

27. The method of claim 25 wherein said composition includes a penetrating agent.

28. The method of claim 25 wherein said composition is admixed with a pharmaceutically acceptable cream, lotion, gel or liquid vehicle prior to being administered.

29. A method of enhancing the formation of protective scabs over wounds in horses, comprising: administering to a horse wound a therapeutically effective amount of a composition comprising a derivative of Glycyl-L-Histidyl-L-Lysine: Copper(II) having the general formula:

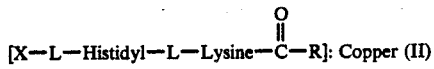

wherein X is glycyl-L-alanyl, glycyl-L-seryl, glycyl-L-valyl, or glycyl-L-glycyl, and where R is selected from the group consisting of alkyl moieties containing from 1 to 18 carbon atoms, aryl moieties containing from 6 to 12 carbon atoms, alkoxy moieties containing from 1 to 18 carbon atoms, or wherein R is L-prolyl-L-phenylalanyl-L-valine or L-valyl-L-phenylalanyl-L-valine.

30. The method of claim 29 wherein said composition includes an emulsifying or surface active agent.

31. The method of claim 29 wherein said composition includes a penetrating agent.

32. The method of claim 29 wherein said composition is admixed with a pharmaceutical acceptable cream, lotion, gel or liquid vehicle prior to being administered.

* * * * *

UNITED STATES PATENT AND TRADEMARK OFFICE
CERTIFICATE OF CORRECTION

PATENT NO. : 4,937,230

DATED : June 26, 1990

INVENTOR(S) : Loren R. Pickart

It is certified that error appears in the above-identified patent and that said Letters Patent is hereby corrected as shown below:

In claim 9, at column 11, line 39, delete "(II)"; and at line 40, delete "Cooper" and substitute therefor --Copper (II)--.

In claim 17, at column 12, line 22, delete "(II)"; and at line 23, delete "Cooper" and substitute therefor --Copper (II)--.

In claim 25, at column 13, line 6, delete "(II)"; and at line 7, delete "Cooper" and substitute therefor --Copper (II)--.

In claim 32, at column 14, line 23, delete "pharmaceutical" and substitute therefor --pharmaceutically--.

Signed and Sealed this

Fifth Day of November, 1991

Attest:

HARRY F. MANBECK, JR.

*Attesting Officer*     *Commissioner of Patents and Trademarks*